US008044252B2

(12) United States Patent
Nappa et al.

(10) Patent No.: US 8,044,252 B2

(45) Date of Patent: Oct. 25, 2011

(54) CATALYTIC ISOMERIZATION BETWEEN E AND Z ISOMERS OF 1,2,3,3,3-PENTAFLUOROPROPENE

(75) Inventors: Mario Joseph Nappa, Newark, DE (US); Donald J. Toton, New Castle, DE (US); Velliyur Nott Mallikarjuna Rao, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 274 days.

(21) Appl. No.: 12/373,588

(22) PCT Filed: Jul. 11, 2007

(86) PCT No.: PCT/US2007/015752

§ 371 (c)(1), (2), (4) Date: Feb. 23, 2009

(87) PCT Pub. No.: WO2008/008351

PCT Pub. Date: Jan. 17, 2008

(65) Prior Publication Data

US 2010/0010277 A1 Jan. 14, 2010

Related U.S. Application Data

(60) Provisional application No. 60/830,940, filed on Jul. 13, 2006.

(51) Int. Cl.
*C07C 17/00* (2006.01)

(52) U.S. Cl. ........................................................ 570/236

(58) Field of Classification Search ................... 570/236
See application file for complete search history.

(56) References Cited

U.S. PATENT DOCUMENTS

| | | | | |
|---|---|---|---|---|
| 3,398,204 | A * | 8/1968 | Gallant | 570/236 |
| 3,914,167 | A * | 10/1975 | Ivy et al. | 204/157.98 |
| 4,978,649 | A | 12/1990 | Surovikin et al. | |
| 5,136,113 | A | 8/1992 | Rao | |
| 5,268,122 | A | 12/1993 | Rao et al. | |

FOREIGN PATENT DOCUMENTS

| | | |
|---|---|---|
| WO | 9833755 A1 | 8/1998 |

OTHER PUBLICATIONS

Burton D J et al: "Preparation of E-1,2,3,3,3-Pentafluoropropene, Z-1,2,3,3,3-Pentafluoropropene and E-1-Iodopentafluoropropene", Journal of Fluorine Chemistry, Elsevier, Amsterdam, NL, vol. 44, No. 1, Jul. 1, 1989, pp. 167-174, Lausanne, CH, XP000008378, p. 167, second equation; p. 169, "Preparation of Z-1,2,3,3,3-pentafluoropropene".

Clot, Eric et al: "Defluorination of Perfluoropropene Using Cp2ZrH2 and Cp2ZrHF: A Mechanism Investigation from a Joint Experimental-Theoretical Perspective", Journal of the American Chemical Society, vol. 126, No. 17, 2004, pp. 5647-5653, XP002459919, p. 5648, "equation (4)".

Heng-Dao Quan et al: "SbF5/PAF-a novel fluorinating reagent in preparing fluorine compounds", Journal of Fluorine Chemistry, Elsevier, 125 (2004) pp. 1169-1172.

Prog. Solid St. Chem., vol. 26, pp. 97-153, "Fluorinated Metal Oxides and Metal Fluorides As Heterogeneous Catalysts", Dr. Erhard Kemnitz and Dr. Dirk Henning Menz, Elsevier Science Ltd, Great Britain, 1998.

* cited by examiner

*Primary Examiner* — Jafar Parsa

(57) ABSTRACT

A process is disclosed to increase the Z/E ratio of 1,2,3,3,3-pentafluoropropene. The process involves contacting a starting material comprising 1,2,3,3,3-pentafluoropropene with a catalyst on $AlF_3$ or carbon, wherein the catalyst is selected from the group consisting of $SbCl_wF_{5-w}$, $TiCl_xF_{4-x}$, $SnCl_yF_{4-y}$ and $TaCl_zF_{5-z}$ wherein w is from 0 to 4, x is from 0 to 3, y is from 0 to 3, z is from 0 to 4, to obtain a product wherein the Z/E ratio of 1,2,3,3,3-pentafluoropropene is increased relative to the Z/E ratio of 1,2,3,3,3-pentafluoropropene in the starting material.

A process is also disclosed to decrease the Z/E ratio of 1,2,3,3,3-pentafluoropropene. The process involves contacting a starting material comprising 1,2,3,3,3-pentafluoropropene with a catalyst on $AlF_3$ or carbon, wherein the catalyst is selected from the group consisting of $SbCl_wF_{5-w}$, $TiCl_xF_{4-x}$, $SnCl_yF_{4-y}$ and $TaCl_zF_{5-z}$ wherein w is from 0 to 4, x is from 0 to 3, y is from 0 to 3, z is from 0 to 4, to obtain a product wherein the Z/E ratio of 1,2,3,3,3-pentafluoropropene is decreased relative to the Z/E ratio of 1,2,3,3,3-pentafluoropropene in the starting material.

15 Claims, No Drawings

CATALYTIC ISOMERIZATION BETWEEN E AND Z ISOMERS OF 1,2,3,3,3-PENTAFLUOROPROPENE

This application represents a national filing under 35 U.S.C. 371 of International Application No. PCT/US2007/015752 filed Jul. 11, 2007, and claims priority of U.S. Provisional Application No. 60/830,940 filed Jul. 13, 2006.

BACKGROUND

1. Field of the Disclosure

The disclosure herein relates in general to processes for the catalytic isomerization between E and Z isomers of 1,2,3,3,3-pentafluoropropene (HFC-1225ye).

2. Description of Related Art

As a result of the Montreal Protocol phasing out ozone depleting chlorofluorocarbons (CFCs) and hydrochlorofluorocarbons (HCFCs), industry has been working for the past few decades to find replacement refrigerants. The solution for most refrigerant producers has been the commercialization of hydrofluorocarbon (HFC) refrigerants. The new hydrofluorocarbon refrigerants, HFC-134a being the most widely used at this time, have zero ozone depletion potential and thus are not affected by the current regulatory phase out as a result of the Montreal Protocol. The production of other hydrofluorocarbons for use in applications such as solvents, blowing agents, cleaning agents, aerosol propellants, heat transfer media, dielectrics, fire extinguishants and power cycle working fluids has also been the subject of considerable interest.

There is also considerable interest in developing new refrigerants with reduced global warming potential for the mobile air-conditioning market.

HFC-1225ye, having zero ozone depletion and a low global warming potential, has been identified as a potential refrigerant. HFC-1225ye can also find use in other applications such as solvents, cleaning agents, foam blowing agents, aerosol propellants, heat transfer media, dielectrics, fire extinguishing agents, sterilants and power cycle working fluids. HFC-1225ye may also be used to make polymers. HFC-1225ye may exist as one of two configurational isomers, E or Z, which boils at different temperatures. Depending on the applications, HFC-1225ye may be preferably used as a Z isomer or a E isomer or a mixture thereof. The liquid phase $SbF_5$ catalyzed isomerization of E-HFC-1225ye to Z-HFC-1225ye has been described by Burton et al. in Journal of Fluorine Chemistry, 44, 167-174 (1989).

There is a need for new catalytic isomerization processes for the isomerization between E-HFC-1225ye and Z-HFC-1225ye.

SUMMARY

A process has been provided to increase the Z/E ratio of HFC-1225ye. The process comprises: contacting a starting material comprising HFC-1225ye with a catalyst supported on $AlF_3$ or carbon, wherein said catalyst is selected from the group consisting of $SbCl_wF_{5-w}$, $TiCl_xF_{4-x}$, $SnCl_yF_{4-y}$ and $TaCl_zF_{5-z}$ wherein w is from 0 to 4, x is from 0 to 3, y is from 0 to 3, z is from 0 to 4, to obtain a product wherein the Z/E ratio of HFC-1225ye is increased relative to the Z/E ratio of HFC-1225ye in said starting material.

A process has also been provided to decrease the Z/E ratio of HFC-1225ye. The process comprises: contacting a starting material comprising HFC-1225ye with a catalyst supported on $AlF_3$ or carbon, wherein said catalyst is selected from the group consisting of $SbCl_wF_{5-w}$, $TiCl_xF_{4-x}$, $SnCl_yF_{4-y}$ and $TaCl_zF_{5-z}$ wherein w is from 0 to 4, x is from 0 to 3, y is from 0 to 3, z is from 0 to 4, to obtain a product wherein the Z/E ratio of HFC-1225ye is decreased relative to the Z/E ratio of HFC-1225ye in said starting material.

If the olefin is made at high temperature using a catalyst that will equilibrate the two, then they will be made as a mixture with the ratio of the two depending on the temperature at which they were made. If you have a catalyst to interconvert one to the other you can change the ratio by changing the temperature. For example, if you start with pure Z and you want to make E, you can equilibrate them at 350° C. and make about 10% E. If you start at 10% E, which is the case when we make the two at 350° C., you can increase the Z to 99% by interconverting them at 25° C. using the claimed catalyst. Therefore, you can approach the equilibrium composition from either side.

The foregoing general description and the following detailed description are exemplary and explanatory only and are not restrictive of the invention, as defined in the appended claims.

DETAILED DESCRIPTION

Before addressing details of embodiments described below, some terms are defined or clarified.

HFC-1225ye may exist as one of two configurational isomers, E or Z. HFC-1225ye as used herein refers to the isomers, E-HFC-1225ye (CAS reg no. 5595-10-8) or Z-HFC-1225ye (CAS reg. no. 5528-43-8), as well as any combinations or mixtures of such isomers.

The term "Z/E ratio" is intended to mean the molar ratio of Z isomer to E isomer of an olefin. For example, the term "Z/E ratio of HFC-1225ye" is intended to mean the molar ratio of Z-HFC-1225ye to E-HFC-1225ye.

The term "an elevated temperature" is intended to mean a temperature higher than room temperature.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

A process has been provided to increase the Z/E ratio of 1,2,3,3,3-pentafluoropropene. The process comprises: contacting a starting material comprising 1,2,3,3,3-pentafluoropropene with a catalyst on $AlF_3$ or carbon, wherein said catalyst is selected from the group consisting of $SbCl_wF_{5-w}$, $TiCl_xF_{4-x}$, $SnCl_yF_{4-y}$ and $TaCl_zF_{5-z}$ wherein w is from 0 to 4, x is from 0 to 3, y is from 0 to 3, z is from 0 to 4, to obtain a product wherein the Z/E ratio of 1,2,3,3,3-pentafluoropropene is increased relative to the Z/E ratio of 1,2,3,3,3-pentafluoropropene in said starting material.

A process has also been provided to decrease the Z/E ratio of 1,2,3,3,3-pentafluoropropene. The process comprises: contacting a starting material comprising 1,2,3,3,3-pentafluoropropene with a catalyst on $AlF_3$ or carbon, wherein said catalyst is selected from the group consisting of $SbCl_wF_{5-w}$, $TiCl_xF_{4-x}$, $SnCl_yF_{4-y}$ and $TaCl_zF_{5-z}$ wherein w is from 0 to 4, x is from 0 to 3, y is from 0 to 3, z is from 0 to 4, to obtain a product wherein the Z/E ratio of 1,2,3,3,3-pentafluoropropene is decreased relative to the Z/E ratio of 1,2,3,3,3-pentafluoropropene in said starting material.

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims.

$AlF_3$ can be made according to Journal of Fluorine Chemistry, 125, 1169-1172 (2004), which is incorporated herein by reference.

Carbon from any of the following sources are useful for the embodiments of this invention: wood, peat, coal, coconut shells, bones, lignite, petroleum-based residues and sugar. Commercially available carbons which may be used include those sold under the following trademarks: Barneby & Sutcliffe™, Darco™, Nucharm, Columbia JXN™, Columbia LCK™, Calgon PCB, Calgon BPL™, Westvaco™, Norit™, and Barnaby Cheny NB™.

Carbon includes unwashed and acid-washed carbon (e.g., carbon which has been treated with hydrochloric acid or hydrochloric acid followed by hydrofluoric acid). Acid treatment is typically sufficient to provide carbon that contains less than 1000 ppm of ash. Suitable acid treatment of carbon is described in U.S. Pat. No. 5,136,113, incorporated herein by reference. The carbon also includes three dimensional matrix porous carbonaceous materials. Examples are those described in U.S. Pat. No. 4,978,649, incorporated herein by reference. In one embodiment of the invention, carbon includes three dimensional matrix carbonaceous materials which are obtained by introducing gaseous or vaporous carbon-containing compounds (e.g., hydrocarbons) into a mass of granules of a carbonaceous material (e.g., carbon black); decomposing the carbon-containing compounds to deposit carbon on the surface of the granules; and treating the resulting material with an activator gas comprising steam to provide a porous carbonaceous material. A carbon-carbon composite material is thus formed.

Preparation of $SbF_5$ on $AlF_3$ has been described by Quan et al. in Journal of Fluorine Chemistry, 125, 1169-1172 (2004).

Preparation of $SbCl_wF_{5-w}$, on $AlF_3$ is generally described in Examples 1 and 2. Preparation of $TiCl_xF_{4-x}$ on $AlF_3$ is generally described in Example 3. Preparation of $SnCl_yF_{4-y}$ on $AlF_3$ is generally described in Example 4. Preparation of $TaCl_zF_{5-z}$ on $AlF_3$ is generally described in Example 5.

Preparation of $SbCl_wF_{5-w}$ on carbon is generally described in Examples 6 and 7. Preparation of $TiCl_xF_{4-x}$ on carbon is generally described in Example 8. Preparation of $SnCl_yF_{4-y}$ on carbon is generally described in Example 9. Preparation of $TaCl_zF_{5-z}$ on carbon is generally described in Example 10.

The contact time of HFC-1225ye with the catalyst typically ranges from about 1 second to 1 hour. In one embodiment of the invention, the contact time ranges from about 5 seconds to 60 seconds.

The pressure employed in the isomerization process can be subatmospheric, atmospheric or superatmospheric. In one embodiment of the invention, the isomerization pressure is near atmospheric. In another embodiment of the invention, the isomerization pressure is autogenous.

The reactor for the isomerization process and its associated feed lines, effluent lines, and associated units used in applying the processes of embodiments of this invention should be constructed of materials resistant to corrosion. Typical materials of construction include stainless steels, in particular of the austenitic type, the well-known high nickel alloys, such as Monel™ nickel-copper alloys, Hastelloy™ nickel-based alloys and, Inconel™ nickel-chromium alloys, and copper-clad steel.

In a process to increase the Z/E ratio of HFC-1225ye, the HFC-1225ye in the starting material is either E-HFC-1225ye or a mixture of E-HFC-1225ye and Z-HFC-1225ye. The HFC-1225ye in the starting material has a lower Z/E ratio than the HFC-1225ye in the product.

In a process to increase the Z/E ratio of HFC-1225ye, the temperature employed typically ranges from about −20° C. to about 150° C. In one embodiment of the invention, the temperature employed in the process to increase the Z/E ratio of HFC-1225ye ranges from about −10° C. to 100° C. In another embodiment of the invention, the temperature employed in the process to increase the Z/E ratio of HFC-1225ye ranges from about 0° C. to 50° C. In another embodiment of the invention, the process to increase the Z/E ratio of HFC-1225ye is conducted at about room temperature.

In a process to increase the Z/E ratio of HFC-1225ye, the product has a higher Z/E ratio of HFC-1225ye than the starting material. In one embodiment of the invention, the Z/E ratio of HFC-1225ye in the product is at least 10. In another embodiment of the invention, the Z/E ratio of HFC-1225ye in the product is at least 20. In another embodiment of the invention, the Z/E ratio of HFC-1225ye in the product is at least 40.

In a process to decrease the Z/E ratio of HFC-1225ye, the HFC-1225ye in the starting material is either Z-HFC-1225ye or a mixture of E-HFC-1225ye and Z-HFC-1225ye. The HFC-1225ye in the starting material has a higher Z/E ratio than the HFC-1225ye in the product.

In a process to decrease the Z/E ratio of HFC-1225ye, the process is typically conducted at an elevated temperature. In one embodiment of the invention, the process is conducted at a temperature from about 300° C. to 450° C. Without wishing to be bound by the theory, it is understood that the isomerization between E-HFC-1225ye and Z-HFC-1225ye is an equilibrium reaction. It is also understood that Z-HFC-1225ye is thermodynamically more stable than E-HFC-1225ye, and the Z/E ratio can be increased by decreasing the temperature in presence of the claimed catalysts.

EXAMPLES

The concepts described herein will be further described in the following examples, which do not limit the scope of the invention described in the claims.

Examples 1-10 demonstrate the preparation of the catalysts.

Example 1

Example 1 demonstrates the preparation of $SbCl_wF_{5-w}$ (w=0 to 4) on $AlF_3$. Twenty five grams of $AlF_3.3H_2O$ (12/20 mesh) is heated for 10 hours at 300° C. under a purge of nitrogen (10 sccm, $1.7\times10^{-7}$ $m^3/s$). Under an inert atmosphere, the $AlF_3$ is transferred to a glass round bottom flask and 25 gm of $SbCl_5$ is slowly dripped onto the powder. Periodic mixing with a Teflon® paddle is carried out to infuse the mixture. Under an inert atmosphere, the $SbCl_5$ on $AlF_3$ is transferred to ⅝" Inconel tube for treatment with HF. The catalyst is heated under a flow of nitrogen (20 sccm, $3.3\times10^{-7}$ $m^3/s$) for three hours at 100° C. Anhydrous HF (50 sccm, $6.0\times10^{-7}$ $m^3/s$) and $N_2$ (50 sccm, $6.0\times10^{-7}$ $m^3/s$) are passed over the catalyst at 200° C. for 2 hours and then only HF (100 sccm, $1.2\times10^{-6}$ $m^3/s$) for 3 hours. The temperature is lowered to ambient and $N_2$ (50 sccm, $6.0\times10^{-7}$ $m^3/s$) is passed over the catalyst for 8 hours.

Example 2

Example 2 demonstrates the preparation of $SbCl_wF_{5-w}$ (w=0 to 4) on $AlF_3$. This catalyst is prepared as described in Example 1 except 18.3 gm of $SbF_5$ are used in place of the $SbCl_5$ and HF treatment is optional Example 3

Example 3 demonstrates the preparation of $TiCl_xF_{4-x}$ (x=0 to 3) on $AlF_3$. This catalyst is prepared as described in Example 1 except 15.9 gm of $TiCl_4$ is used instead of $SbCl_5$.

Example 4

Example 4 demonstrates the preparation of $SnCl_yF_{4-y}$ (y=0 to 3) on $AlF_3$. This catalyst is prepared as described in Example 1 except 22.0 gm of $SnCl_4$ is used instead of $SbCl_5$.

Example 5

Example 5 demonstrates the preparation of $TaCl_2F_{5-z}$ (z=0 to 4) on $AlF_3$. $AlF_3$ pellets (20 gm) ground to 12/20 mesh are dried in a flow of $N_2$ (50 sccm, $6.0\times10^{-7}$ $m^3/s$) for 10 hours at 300° C. Under an inert atmosphere, the pellets are transferred to a 1 L Hastelloy C rocker bomb containing $TaCl_5$ (30.1 gm). The rocker bomb is cooled and anhydrous HF (200 gm) is added via vacuum transfer. The mixture is heated to 50° C. for four hours while rocking and then the HF and HCl are vented to a scrubber. Under a nitrogen blanket the solid is removed from the rocker bomb and transferred to the Inconel reactor described in Example 1. Anhydrous HF (50 sccm, $6.0\times10^{-7}$ $m^3/s$) and $N_2$ (50 sccm, $6.0\times10^{-7}$ $m^3/s$) are passed over the catalyst at 80° C. for 2 hours and then only HF (100 sccm, $1.2\times10^{-6}$ $m^3/s$) for 3 hours. The temperature is lowered to ambient and $N_2$ (50 sccm, $6.0\times10^{-7}$ $m^3/s$) is passed over the catalyst for 8 hours.

Example 6

Example 6 demonstrates the preparation of $SbCl_wF_{5-w}$ (w=0 to 4) on carbon. Acid washed coconut shell carbon (6×10 mesh, 10 gm) as described in U.S. Pat. No. 5,136,113 is heated for 10 hours at 300° C. under a purge of nitrogen (10 sccm, $1.7\times10^{-7}$ $m^3/s$). Under an inert atmosphere, the carbon particles are transferred to a glass round bottom flask and 25 gm of $SbCl_5$ is slowly dripped onto the powder. Periodic mixing with a Teflon® paddle is carried out to infuse the mixture. Under an inert atmosphere, the $SbCl_5$ on carbon is transferred to ⅝" Inconel tube for treatment with HF. The catalyst is heated under a flow of nitrogen (20 sccm, $3.3\times10^{-7}$ $m^3/s$) for three hours at 100° C. Anhydrous HF (50 sccm, $6.0\times10^{-7}$ $m^3/s$) and $N_2$ (50 sccm, $6.0\times10^{-7}$ $m^3/s$) are passed over the catalyst at 200° C. for 2 hours and then only HF (100 sccm, $1.2\times10^{-6}$ $m^3/s$) for 3 hours. The temperature was lowered to ambient and $N_2$ (50 sccm, $6.0\times10^{-7}$ $m^3/s$) was passed over the catalyst for 8 hours.

Example 7

Example 7 demonstrates the preparation of $SbCl_wF_{5-w}$ (w=0 to 4) on carbon. This catalyst is prepared as described in Example 6 except 18.3 gm of $SbF_5$ are used in place of the $SbCl_5$ and HF treatment is not required.

Example 8

Example 8 demonstrates the preparation of $TiCl_xF_{4-x}$ (x=0 to 3) on carbon. This catalyst is prepared as described in Example 6 except 15.9 gm of $TiCl_4$ is used instead of $SbCl_5$.

Example 9

Example 9 demonstrates the preparation of $SnCl_yF_{4-y}$ (y=0 to 3) on $AlF_3$. This catalyst is prepared as described in Example 6 except 22.0 gm of $SnCl_4$ is used instead of $SbCl_5$.

Example 10

Example 10 demonstrates the preparation of $TaCl_zF_{5-z}$ (z=0 to 4) on carbon. Acid washed coconut shell carbon (6×10 mesh, 10 gm) as described in U.S. Pat. No. 5,136,113 is dried in a flow of $N_2$ (50 sccm, $6.0\times10^{-7}$ $m^3/s$) for 10 hours at 300° C. Under an inert atmosphere, the particles are transferred to a 1 L Hastelloy C rocker bomb containing $TaCl_5$ (30.1 gm). The rocker bomb is cooled and anhydrous HF (200 gm) is added via vacuum transfer. The mixture is heated to 50° C. for four hours while rocking and then the HF and HCl are vented to a scrubber. Under a nitrogen blanket the solid is removed from the rocker bomb and transferred to the Inconel reactor described in Example 1. Anhydrous HF (50 sccm, $6.0\times10^{-7}$ $m^3/s$) and $N_2$ (50 sccm, $6.0\times10^{-7}$ $m^3/s$) are passed over the catalyst at 80° C. for 2 hours and then only HF (100 sccm, $1.2\times10^{-6}$ $m^3/s$) for 3 hours. The temperature is lowered to ambient and $N_2$ (50 sccm, $6.0\times10^{-7}$ $m^3/s$) is passed over the catalyst for 8 hours.

Examples 11-18 describe the isomerization processes of HFC-1225ye in the presence of the catalysts.

Example 11

Example 11 demonstrates the isomerization of E-HFC-1225ye to Z-HFC-1225ye.

To a 15"×⅝" OD Inconel reactor is added 10 cc of $SbX_5$ (where X is Cl or F) on $AlF_3$ prepared as described in Example 1. E-HFC-1225ye (20 sccm, $3.3\times10^{-7}$ $m^3/s$) is passed over the catalyst at room temperature, and the reactor effluent is analyzed by GC-MS and found to contain Z-HFC-1225ye.

Example 12

This is similar to Example 11 except $TiX_4$ catalyst is used as described in Example 3.

Example 13

This is similar to Example 11 except $SnX_4$ catalyst is used as described in Example 4.

Example 14

This is similar to Example 11 except $TaX_5$ catalyst is used as described in Example 5.

Example 15

This is similar to Example 11 except $SbX_5$ catalyst is used as described in Example 7.

Example 16

This is similar to Example 11 except $TiX_4$ catalyst is used as described in Example 8.

Example 17

This is similar to Example 11 except $SnX_4$ catalyst is used as described in Example 9.

Example 18

This is similar to Example 11 except $TaX_5$ catalyst is used as described in Example 10.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

What is claimed is:

1. A process comprising: contacting a starting material comprising 1,2,3,3,3-pentafluoropropene with a catalyst supported on $AlF_3$ or carbon, wherein said catalyst is selected from the group consisting of $SbCl_wF_{5-w}$, $TiCl_xF_{4-x}$, $SnCl_yF_{4-y}$ and $TaCl_zF_{5-z}$ wherein w is from 0 to 4, x is from 0 to 3, y is from 0 to 3, z is from 0 to 4, to obtain a product wherein the Z/E ratio of 1,2,3,3,3-pentafluoropropene is increased relative to the Z/E ratio of 1,2,3,3,3-pentafluoropropene in said starting material.

2. The process of claim 1 wherein the Z/E ratio of 1,2,3,3,3-pentafluoropropene in said product is at least 10.

3. The process of claim 1 wherein 1,2,3,3,3-pentafluoropropene in said starting material is E-1,2,3,3,3-pentafluoropropene.

4. The process of claim 1 wherein said contact is conducted at a temperature of from about −20° C. to about 150° C.

5. A process comprising: contacting a starting material comprising 1,2,3,3,3-pentafluoropropene with a catalyst supported on $AlF_3$ or carbon, wherein said catalyst is selected from the group consisting of $SbCl_wF_{5-w}$, $TiCl_xF_{4-x}$, $SnCl_yF_{4-y}$ and $TaCl_zF_{5-z}$ wherein w is from 0 to 4, x is from 0 to 3, y is from 0 to 3, z is from 0 to 4, to obtain a product wherein the Z/E ratio of 1,2,3,3,3-pentafluoropropene is decreased relative to the Z/E ratio of 1,2,3,3,3-pentafluoropropene in said starting material.

6. The process of claim 5 wherein 1,2,3,3,3-pentafluoropropene in said starting material is Z-1,2,3,3,3-pentafluoropropene.

7. The process of claim 5 wherein said contact is conducted at a temperature of from about 300° C. to about 450° C.

8. The process of claim 1 wherein said catalyst is $SbF_5$.

9. The process of claim 1 wherein said catalyst is $TiCl_xF_{4-x}$, wherein x is from 0 to 3.

10. The process of claim 1 wherein said catalyst is $SnCl_yF_{4-y}$, wherein w is from 0 to 3.

11. The process of claim 1 wherein said catalyst is $TaCl_zF_{5-z}$ wherein z is from 0 to 4.

12. The process of claim 5 wherein said catalyst is $SbF_5$.

13. The process of claim 5 wherein said catalyst is $TiCl_xF_{4-x}$, wherein x is from 0 to 3.

14. The process of claim 5 wherein said catalyst is $TaCl_zF_{5-z}$ wherein z is from 0 to 4.

15. The process of claim 5 wherein said catalyst is $SnCl_yF_{4-y}$, wherein w is from 0 to 3.

* * * * *